United States Patent
Sarkela et al.

(10) Patent No.: US 10,413,254 B2
(45) Date of Patent: Sep. 17, 2019

(54) DYNAMIC AUTOMATED ADJUSTMENT OF ALARM THRESHOLD LEVELS

(71) Applicant: General Electric Company, Schenectady, NY (US)

(72) Inventors: Mika Sarkela, Helsinki (FI); Rene Johannes Coffeng, Helsinki (FI); Kimmo Uutela, Helsinki (FI); Liisa-Maria Järvelä, Helsinki (FI)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 15/205,514

(22) Filed: Jul. 8, 2016

(65) Prior Publication Data
US 2018/0008207 A1 Jan. 11, 2018

(51) Int. Cl.
*A61B 5/00* (2006.01)
*G06F 19/00* (2018.01)
(Continued)

(52) U.S. Cl.
CPC ............ *A61B 5/746* (2013.01); *A61B 5/7282* (2013.01); *A61B 5/742* (2013.01); *A61B 5/7405* (2013.01);
(Continued)

(58) Field of Classification Search
CPC ....... A61B 5/746; A61B 5/0215; A61B 5/026; A61B 5/0816; A61B 5/14542;
(Continued)

(56) References Cited

U.S. PATENT DOCUMENTS

| 9,028,407 B1* | 5/2015 | Bennett-Guerrero ....... A61B 5/1121 224/929 |
| 2003/0025604 A1* | 2/2003 | Freeman ............ A61B 5/7475 340/573.1 |

(Continued)

FOREIGN PATENT DOCUMENTS

| EP | 2256495 A2 | 12/2010 |
| WO | 2015101891 A1 | 7/2015 |

OTHER PUBLICATIONS

International Search Report and Written Opinion for PCT/US2017/039755, dated Sep. 29, 2017, 11 pages.

*Primary Examiner* — Quan-Zhen Wang
*Assistant Examiner* — Rajsheed O Black-Childress
(74) *Attorney, Agent, or Firm* — Boyle Fredrickson, S.C.

(57) ABSTRACT

In the present invention, a system and associated method is provided for monitoring vital parameters of a patient. The monitoring system includes sensors disposed on the patient and operably connected to a monitor. The parameters that are sensed by the sensors are transmitted to the monitor and compared with alarm thresholds stored within the monitor. The alarm thresholds stored within the monitor are modified by inputs supplied to the monitor regarding the particular condition(s) of the patient being monitored to provide more accurate alarm determinations for the patient. The dynamic adjustment of the alarm threshold during monitoring can be based on a set of proactive inputs to prevent and/or limit the occurrence of unnecessary or clinically irrelevant alarm conditions or a set of reactive inputs that follow immediately after an alarm event is detected, to enable medical personnel to appropriately respond to sensed alarm condition(s).

20 Claims, 2 Drawing Sheets

(51) Int. Cl.
*G16H 40/63* (2018.01)
*A61B 5/0215* (2006.01)
*A61B 5/026* (2006.01)
*A61B 5/08* (2006.01)
*A61B 5/145* (2006.01)

(52) U.S. Cl.
CPC ......... *G06F 19/3418* (2013.01); *G16H 40/63* (2018.01); *A61B 5/026* (2013.01); *A61B 5/0215* (2013.01); *A61B 5/0816* (2013.01); *A61B 5/14542* (2013.01)

(58) Field of Classification Search
CPC ..... A61B 5/7282; A61B 5/7405; A61B 5/742; G06F 19/3418; G16H 40/63
See application file for complete search history.

(56) References Cited

U.S. PATENT DOCUMENTS

| | | | |
|---|---|---|---|
| 2008/0058773 A1* | 3/2008 | John | G16H 50/20 604/891.1 |
| 2009/0247848 A1 | 10/2009 | Baker, Jr. | |
| 2009/0247851 A1 | 10/2009 | Batchelder et al. | |
| 2011/0140896 A1 | 6/2011 | Menzel | |
| 2012/0323086 A1 | 12/2012 | Hansen | |
| 2013/0340758 A1* | 12/2013 | Schindhelm | A61M 16/0051 128/204.23 |
| 2014/0085076 A1 | 3/2014 | Carnes | |
| 2014/0276549 A1* | 9/2014 | Osorio | A61M 5/1723 604/503 |

\* cited by examiner

DYNAMIC AUTOMATED ADJUSTMENT OF ALARM THRESHOLD LEVELS

BACKGROUND OF THE INVENTION

The invention relates generally to monitoring devices and equipment for obtaining and illustrating data about a patient to which the equipment is connected, and more particularly to monitoring devices and methods for adjusting the thresholds for triggering alarms based on the data from the patient.

In monitoring or diagnostic devices that are currently utilized, the data obtained by the devices is compared to a set limit for the particular physiologic parameter being measured and represented by the incoming data to the device. When the data exceeds the limit, the device is configured, to trigger or set off an alarm in order to indicate the current condition of the patient to a treating physician or other medical care, professional that is monitoring the patient.

However, in many situations the limits or thresholds for the triggering of the alarms are set close to the ranges of normal fluctuations of the values for the parameters being monitored, providing a safety net to prevent adverse events from being missed. As such, even when the parameter value only drops below the alarm limit for an instant due to a non-critical event, the device will trigger an alarm based on that sensed value. While setting the alarm limit in this manner is a safeguard against any significant issue or clinically relevant alarm being missed, as a result of the closeness of the threshold or alarm limit to the normal; or acceptable ranges for this parameter, a large number of clinically irrelevant alarms are generated as well, further, it is not possible to differentiate the clinically relevant alarms from the clinically irrelevant alarms based on the parameter value alone, such that each alarm event must be acted on in the same manner by the medical personnel monitoring the patient.

One result of the large number of the clinically irrelevant alarm events is the unnecessary expenditure of personnel, time and resources in attending to the clinically irrelevant alarm events. Another result is that certain highly important clinical events could inadvertently be overlooked or missed amidst the normally much larger number of clinically irrelevant alarm events. This is often referred to as alarm fatigue and results from the constant representation of the alarm events in a similar manner that can cause certain events to become "lost" in the flood of alarms and associated information represented on the display screen of the particular device. However, while current physiologic limit alarms have a very high false positive rate, setting the limits wider can reduce false positives but at the risk of missing critical, events. Further, the standard alarm limits for many of these devices are often not determined based on the particular condition of the patient being monitored, which can increase the number of clinically irrelevant alarms.

Therefore, in order to address alarm fatigue and reduce the number of clinically irrelevant alarms that are generated, it is desirable to develop a monitoring device and associated alarm adjustment system that operates to adjust the thresholds for alarm generation based on the condition(s) of the particular patient being monitored. Such a device and system would allow for the effective determination of an adverse event using the adjusted threshold, while also allowing for variations in the monitored parameters to limit and/or reduce the number of alarms being triggered for clinically irrelevant events.

BRIEF DESCRIPTION OF THE INVENTION

In various embodiments of the invention, a monitoring device, system and method for monitoring a patient includes a display screen on which data concerning the patient being monitored by the device is illustrated. The incoming data sensed by the device is represented on the display screen to enable an individual viewing the display screen to determine the current physiological, parameters of the patient.

The device and display screen can also illustrate various alarm conditions or events, as determined by the device from the incoming data signals received by the device from sensors attached to the patient being monitored. The alarm conditions or events are triggered by the comparison of parameter limits stored within the device to the incoming data signals from the sensors. In the monitoring system prior to sensing any alarm condition, the system can apply various, proactive inputs supplied by the physician or other medical personnel in order to adjust the alarm threshold for the patient being monitored and prevent/limit the occurrence of any unnecessary or clinically irrelevant alarm event/condition(s). These proactive inputs are supplied by the physician to enable the system to adjust the alarm threshold(s) for the particular patient to better react to the actual condition of the patient being monitored.

Further, after the alarm condition has been sensed, the monitoring system can also utilize reactive inputs that can be determined/selected by the physician for use by the system. These reactive inputs are used by the system after the determination of an alarm event as a check by the monitoring system that the alarm event is an actual actionable alarm event, such as by querying the patient directly to ask about the current condition of the patient.

According to one exemplary embodiment of the invention, a medical monitoring device for providing information about a patient operably connected to the device includes an electronic storage medium in which values for alarm thresholds for a number of physiological parameters to be monitored are stored, a central processing unit operably connected to the electronic storage medium and configured to receive incoming data signals concerning the parameters of the patient and to compare the incoming data signals to the alarm limits for the parameters to determine an alarm condition, one or more sensors operably connected to the central processing unit and adapted to be connected to the patient to obtain and transmit the incoming data signals on the parameters to be monitored from the patient to the central processing, unit and a display operably connected to the central processing unit, the display including a display screen and a user interface configured to enable proactive and reactive inputs to be stored in the electronic storage medium, wherein the central processing unit is configured to dynamically alter the alarm threshold for at least one physiological parameter in response to the proactive and reactive inputs.

According to one exemplary embodiment of the invention, a monitoring device operable to provide information on data obtained from sensors operably connected between a patient and the device includes a central processing unit configured to receive incoming data signals from a sensor connected to the central processing unit concerning a physiological parameter of the patient and to compare the incoming data signals to a predetermined alarm threshold for the physiological parameter to determine an alarm condition and electronic storage media operably connected to the central processing unit and selectively operable to store reactive inputs concerning the adjustment of the alarm threshold for the physiological parameter, wherein the central processing unit is configured to automatically employ the reactive inputs to alter the alarm threshold for the physiological parameter.

According to another exemplary embodiment of the invention, a monitoring device operable to provide information on data obtained from sensors operably connected between a patient and the device includes a central processing unit configured to receive incoming data signals from a sensor connected to the central processing unit concerning a physiological parameter of the patient and to compare the incoming data signals to a predetermined alarm threshold for the physiological parameter to determine an alarm condition, and electronic storage media operably connected to the central processing unit and selectively operable to store proactive inputs concerning the adjustment of the alarm threshold for the physiological parameter, wherein the central processing unit is configured to automatically employ the proactive inputs to alter the alarm threshold for the physiological parameter.

According to still another exemplary embodiment of the invention, a method for dynamically adjusting the alarm limit settings of a monitoring device operable to provide information on data, obtained from sensors operably connected to the device includes the steps of providing the device including a central processing unit configured to receive incoming data signals from a sensor concerning a physiological parameter of a patient and to compare the incoming data signals to a predetermined alarm threshold for the physiological parameters to determine an alarm condition, a user interface operably connected to the central processing unit and electronic storage media operably connected to the central processing unit and adapted to store proactive inputs and reactive inputs from, a user for use in the determination of an alarm condition, inputting at least one of a proactive input and a reactive input into the electronic, storage media, altering the alarm threshold for the physiological parameter in response to the at least one proactive input or reactive input and determining the existence of an alarm indication based on a comparison of the incoming data signals and the altered threshold.

It should be understood that the brief description above is provided to introduce in simplified form a selection, of concepts that are further described in the detailed description, it is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure

BRIEF DESCRIPTION OF THE DRAWINGS

The drawings illustrate the best mode presently contemplated of carrying out the disclosure. In the drawings.

DETAILED DESCRIPTION

In the following detailed description, reference is made to the accompanying drawings that form a part hereof and in which is shown by way of illustration specific embodiments, which may be practiced. These embodiments, are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention disclosed herein relate to a monitoring system and method for monitoring the vital signs of a patient using sensors disposed on the patient and operably connected to a monitor. The vital signs or parameters that are sensed by the sensors are transmitted to the monitor and compared; with alarm thresholds stored within the monitor. The alarm thresholds stored within the monitor are modified by inputs supplied to the monitor regarding the particular condition(s) of the patient being monitored to provide more accurate alarm determinations for the patient. The dynamic automated adjustment of the alarm threshold levels by the monitor during the patient care/monitoring can be based on a set of proactive inputs to prevent and/or limit the occurrence of unnecessary or clinically irrelevant alarm condition(s)/event(s), or a set of reactive inputs that follow immediately after an alarm event is detected, to enable medical personnel to appropriately respond to sensed alarm event(s)/condition(s).

Figure 1:
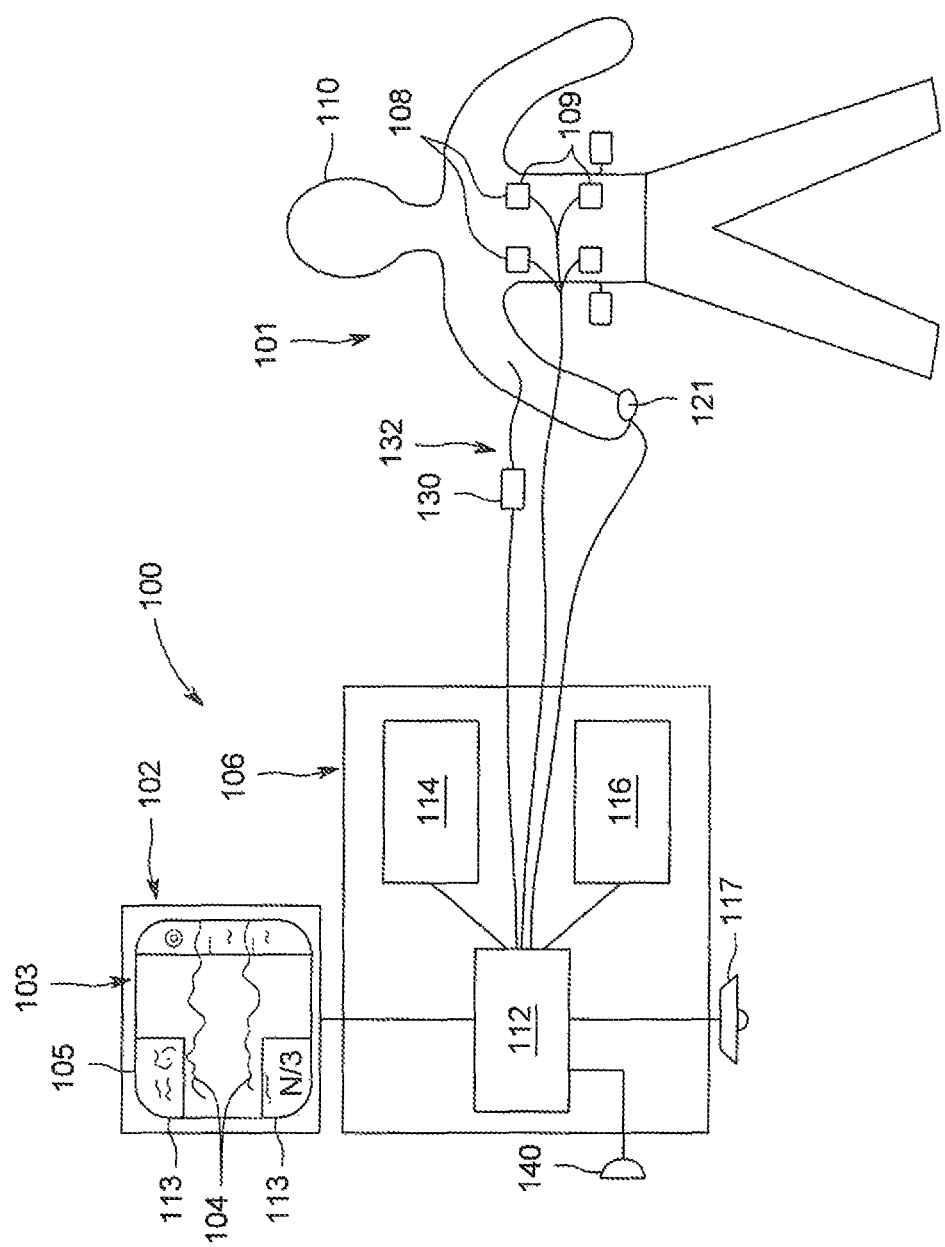
FIG. 1 is a schematic view a patient utilizing a monitoring system according to an exemplary embodiment of the invention.

FIG. 1 illustrates an exemplary embodiment of the invention which Includes a monitoring or diagnostic device and system 100, which can be any suitable type of monitoring device for monitoring various vital signs or parameters of an individual or other item 101 operably connected to the device 100. The device 100 includes a display 102 of any suitable type, such as a touch screen display, having a screen 103 thereon on which the monitoring data signals 104 regarding the object 101 connected to the device 100 can be displayed. When formed as a touch screen, the display 102 can additionally function as a user interface 105 for use in controlling the operation of the device 100, though the interface 105 can be formed as a separate component connected to the device 100, such as a keyboard (not shown) or mouse (not shown) if desired.

In the exemplary embodiment of FIG. 1, the device 100 takes the form of a medical monitoring device 106 that has one or more leads or sensors 108, such as impedance respiration/respiratory sensors 109, operably connected in any suitable manner between the medical monitoring device 106 and a patient 110 in order to monitor various vital statistics of the patient 110. In addition to the sensors 109, the device 100 can employ additional sensors 108 used to monitor other parameters or statistics of the patient 110, such as a pulse oximeter sensor 121 and/or an invasive pressure catheter 130 and invasive pressure transducer 132 to measure the blood flow and pressure of the patient 110 for comparison with the data obtained from the sensors 109, among others.

The medical monitoring device 106 includes a central processing unit (CPU) 112 operably connected to the sensors 108 in order to receive and process data from the sensors 108 on the various vital signs, statistics or parameters of specified bodily functions of the patient 110, which in the exemplary embodiment of FIG. 1 relates to respiratory functions, though other bodily functions or systems are also contemplated as being within the scope of the present invention. These parameter data can then be transmitted from the CPU 112 to the display 102 for presentation in a specified manner on the screen 103 of the display 102 for review by an individual monitoring the patient 110 via the display 102. Alternatively, the CPU 112 can be operably connected, such as by wired or wireless connections, to a network (not shown) that permits the use of multiple visual interfaces (not shown) including those such as a television, health monitor, iPhone or similar device, laptop, portable electronics, among others. This integration of the monitoring device 100 into a system with personal computing devices and portable electronics expands the communication capabilities between clinicians, as well as to facilitate patient observation from remote locations, e.g., central staff stations.

The device 100 also includes memory module 114, which can take the form of any suitable computer-readable electronic storage media, for example a RAM module, and an analytics engine 116, each of which are operably connected to the CPU 112 in order to assist in the monitoring function of the device 100 using the data signals 104 supplied to the CPU 112 via the sensors 108. The device 100 also includes an audio speaker 117 and microphone 140 for enabling the device 100 to provide and receive audible indications of various operating characteristics of the device 100.

The storage media 114 can include certain information regarding the predetermined normal or acceptable ranges for the operating parameters, vital statistics or physiological parameters for the patient 110 to which the device 100 is connected, these stored ranges can be utilized by the CPU 112 in conjunction with the incoming data signals 101 from the sensors 108 and the personal statistics of the patient 110 to determine the current vital statistics or physiological parameters of the patient 110 and whether those vital statistics or physiological parameters are outside of the predetermined ranges for those particular vital statistics or physiological parameters the stored ranges for the incoming data signals 101 on the different physiological parameters and vital statistics received by the CPU 112 from the various sensors 108 can include ranges for minimum and maximum absolute values of the sensed parameters, minimum and maximum frequency ranges for the sensed physiological parameters, or any other suitable aspect of the incoming data signals 104 to be used in the determination of an alarm event or condition.

The storage media 114 can be accessed by a physician utilizing the interface 105 in order to provide or select different proactive and reactive inputs that are to be utilized by the monitoring device 106 with regard to the alarm threshold determination for the patient 110 connected to the monitoring device 106. These inputs are then used by the monitoring device 106 to adjust the thresholds(s) at which various alarms are triggered based on the data on the vital signs/parameters of the patient 110 being sensed by the monitoring device 106. The proactive inputs are supplied directly by the physician to the monitoring device 106 and relate to or reflect the historical and/or background information regarding the patient 110, such as the particular condition that the patient 110 is being treated for or other care/treatment history for the patient 100. These inputs are reflected in changes in the storage media 114 relating to the threshold for one or more of the parameter(s) being monitored by the monitoring device 106 in order to alter the threshold for the triggering of an alarm condition for that parameter prior to any alarm condition being detected or sensed by the monitoring device 106. The proactive inputs are actively utilized by the monitoring device 106 to narrow or raise the threshold level(s) for an alarm condition/event trigger for parameters that are less critical for the patient 110 and/or can widen or lower the threshold level(s) for an alarm condition/event trigger for parameter(s) that are less critical for the patient 110 based on information being sensed by the monitoring device 106. Some examples of these types of proactive inputs stored, in the storage media 114 and used by the CPU 112/analytics engine 116 in the operation of the device 106 include, but are not limited to:

i. Time—concerning the length of stay of a patient after an intervention (lower limits/easier alarm triggering for all or certain selected parameters for the patient 110 during a user-defined initial time period, e.g., three (3) hours, immediately after undergoing any intervention/operation which could prompt user for confirmation of expiration or automatically revert to other more conventional alarm threshold settings upon expiration of the initial time period without an triggered alarm events);
  ii. Time Of The Day—adjust alarm, threshold(s) based on time of day with higher threshold during daytime hours and lower threshold at nighttime, or vice versa;
  iii. Movement—based on history of patient movement decide different threshold(s) for parameter alarms (lower amount of patient movement in recent treatment history results in lower alarm threshold(s), while higher amount of movement in recent treatment history causes higher alarm threshold(s));
  iv. Patient Dynamic Response To Movements
  v. Early Warning Score (EWS)—if the patient 110 has an EWS score over a specified limit defining a high EWS score for the patient 110, the threshold(s) for alarm condition(s) for the patient 110 are lowered, or vice versa if the EWS is low;
  vi. Physical Distance Of Medical Personnel To Patient—closer the patient 110 is to monitoring station (not shown) or individual caregiver/medical personnel (not shown) as determined by location identifier (not shown) carried by individual caregiver/medical personnel the higher the alarm threshold(s) is, and the threshold is lowered the further away the monitoring station or individual caregiver/medical personnel is from the patient 110; (this could optionally be shown, on a central display (not shown) to indicate awareness level to other caregiver/medical personnel);
  vii. Patient Treatment/Diagnoses—the alarm threshold(s) for the monitored parameters relating to the vital organs failing/being treated are lowered, e.g., for a patient 110 being treated for respiratory issues, set tight or lower limits for ventilation related parameter(s), while alarm thresholds for other monitored parameters) remain static or are widened/raised;
  viii. Therapy/Treatment Being Given To Patient 110—alarm threshold(s) for parameters relating to therapy being actively provided to patient 110 by medical personnel, e.g. suctioning, physiotherapy, etc., are lowered.

Thus, with regard to the proactive inputs, the monitoring device 106 can employ the proactive inputs provided or selected by the physician or other medical personnel to dynamically adjust the threshold(s) for various parameters sensed by the monitoring device 106 to prevent and/or limit the occurrence of unnecessary or clinically irrelevant alarm events.

The monitoring device 106 can also receive reactive inputs from the physician or other medical personnel using the device 106. The reactive inputs differ from the proactive inputs in that the reactive inputs do not alter the alarm threshold(s) for any parameter being sensed by the monitoring device 106. Instead the monitoring device 106 employs the reactive inputs either just prior to or after an alarm condition/event has been triggered based upon data sensed by the device 106 and compared against the threshold(s) set within the monitoring device 106, optionally in conjunction with any proactive inputs provided to the monitoring device 106. The reactive inputs are employed to actively solicit a response or reaction from the patient 110 in response to the sensed alarm condition in order to assess the severity or relevancy of the sensed alarm condition. Based on the response received from the patient 110, the device 106 can then make a determination on the nature of the alarm event/condition and whether it requires attention by medical personnel, such as by comparing the response received against a list of potential responses saved in storage media 114 or by employing rules provided to the analytics engine 116 for other decision making purposes. Some examples of these reactive inputs include, but are not limited to:

i. Patient Direct Feedback/Response—when the alarm event is imminent or has been detected, the device 106 will prompt the patient 110 on the display 102 or via the speaker 117 to provide a direct response to the device 106, such as by touching the user interface 105 or another suitable direct response;

ii. Patient Indirect Feedback/Response—the device 106 will prompt the patient 110 on the display 102 or via the speaker 117 to provide a indirect response to the device 106, such as by asking the patient 110 to move via the speaker 117, where the movement confirms patient 110 is breathing;

iii. Telepresence—the medical personnel can directly contact the patient 110 via the device 106, e.g., a video call using the display 102 or through the speaker 117; and inquire about the status or condition of the patient 110 to which the patient 110 can provide a response in a similar manner, such as through the microphone 140 or a communication hub (not shown) that is usable by the patient 110 to provide the response.

Figure 2:
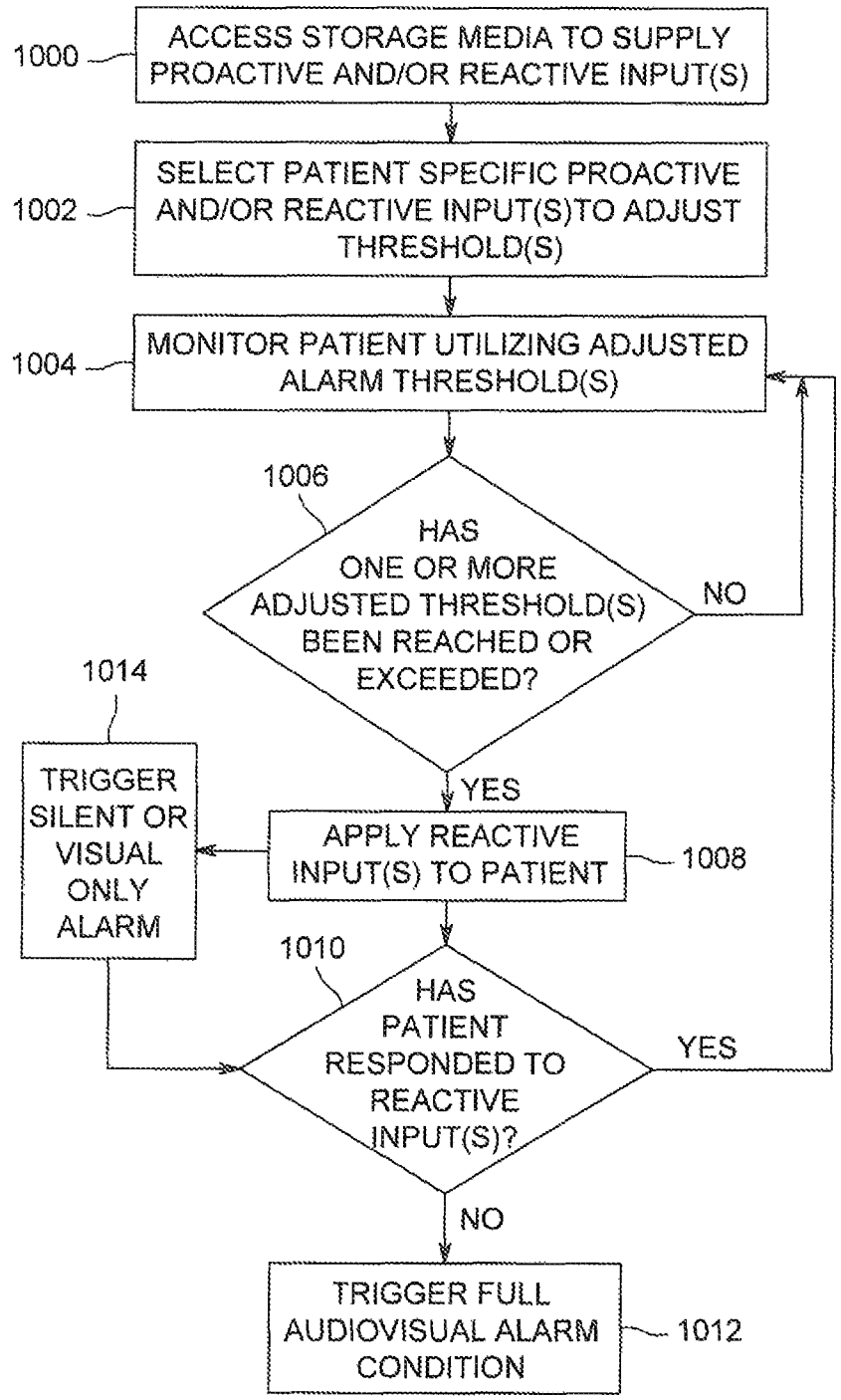
FIG. 2 is a schematic diagram of an embodiment of a method of use of the monitoring system for monitoring a patient according to another exemplary embodiment of the invention.

In an exemplary method associated with the system 100, device 106 and proactive and reactive inputs, as shown in FIG. 2 initially in block 1000 the physician or other medical, personnel will access the storage media 114 in the device 106 using the interlace 105. Depending upon the particular condition of the patient 110 to be monitored, in block 1002 the medical personnel will provide the desired proactive and reactive inputs to the device 106 for storage in the storage media 114 that correspond to the condition(s) and other monitoring/monitored parameters of the patient 110, such as those discussed previously, for use by the device 106 in adjusting the alarm thresholds for the monitored parameters. Then in block 1004 the device 106 actively monitors the patient 110 according to the adjusted alarm thresholds for the monitored parameters as determined by the proactive inputs.

In performing the monitoring function in block 1004, the device 106 uses the proactive inputs stored in the storage media 114 to compare the incoming data from the sensors 108 on the vital signs/parameters of the patient 110 to be sensed. This data is then compared, in decision, block 1006 with the alarm threshold(s) as adjusted by the proactive inputs in order to continually determine if an alarm event has been detected.

If no parameter is reached or exceeded, the system 100 returns to block 1004 to monitor the vital parameters of the patient 110. However, if one of the sensed parameters has reached or exceeded the adjusted threshold for that parameter, in block 1008 the device 106 can proceed to utilize the reactive inputs stored in storage media 114. In accessing these reactive inputs in block 1008 the device 106, under the operational control of the CPU 112 and/or analytics engine 116, provides the selected prompt to the patient 110 in order to assess the current condition of the patient 110 in relation to the sensed alarm event. The device 106 then interprets the response received from the patient 110 in decision block 1010 to determine if the response is sufficient to negate the alarm condition previously sensed, in which case the system 100 returns to block 1004 top continue monitoring the patient 110, or if the response or lack of response requires the alarm condition be confirmed to the appropriate medical personnel, and thus the system 100 triggers an alarm in block 1012.

In addition to the use of the proactive and reactive inputs to provide preventative measures regarding the generation of unnecessary and clinically irrelevant alarms, in another exemplary embodiment the system 100 can segment the alarm event(s)/condition(s) sensed to further limit the generation of unnecessary alarms. More specifically, in the method illustrated in FIG. 3, once an alarm event/condition is determined in block 1006, in conjunction with the employment of the appropriate/selected reactive input in block 1008, in block 1014 the device 106 can provide an indication of an initial or primary alarm condition. This primary or silent alarm condition can be indicated in a visual-only to medical personnel as illustrating the potential for an actual alarm pending a verification of the sensed alarm condition. As such, the initial or primary alarm indication is informational, and does not require attention by medical personnel.

Should the device 106 determine in block 1010 that an actionable alarm event has occurred regarding the patient 110 in block 1010, the system 100/device 106 will alter the alarm indication from a primary alarm to a secondary alarm in block 1012. The secondary alarm provides an audible indication to the medical personnel that the alarm condition has occurred and that attention is required by medical personnel. In this manner, the number of unnecessary or clinically irrelevant alarms is further reduced as a result of the ability of the system 100 to verify the alarm condition utilizing direct or indirect input from the patient 110.

In addition to the previously described exemplary embodiment, the system 100 including the proactive and reactive inputs provided to system 100 inputs for the decisions to make threshold changes can be applied to systems 100 that employ monitoring devices worn by the patient (not shown) and different systems 100 having sensors 108 and hubs (not shown) in the control of the patient 110.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for dynamically adjusting the alarm limit settings of a monitoring device operable to provide information on data obtained from sensors operably connected to the device, the method comprising the steps of:

a. providing the device including a central processing unit configured to receive incoming data signals from sensors concerning multiple physiological parameters of a patient and to directly compare the incoming data signals to a predetermined alarm threshold for the each of the physiological parameters to determine an alarm condition based on one or more of the alarm thresholds, a user interface operably connected to the central processing unit and electronic storage media operably connected to the central processing unit and adapted to store proactive inputs and reactive inputs from a user for use in the determination of an alarm condition;

b. inputting at least one proactive input into the electronic storage media;

c. inputting at least one reactive input into the electronic storage media;

d. altering the alarm threshold for each individual physiological parameter in response to the at least one proactive input;

e. determining the existence of an alarm condition based on a comparison of the incoming data signals and the altered threshold; and f. verifying the alarm condition by employing the at least one reactive input with the patient.

2. The method of claim 1 wherein the step of altering the alarm threshold comprises raising or lowering the alarm threshold for a predetermined time period.

3. The method of claim 2 wherein the predetermined time period is a selected period of time following a procedure on the patient.

4. The method of claim 2 wherein the predetermined time period is selected from daylight or nighttime hours, or a combination thereof.

5. The method of claim 1 wherein the step of altering the alarm threshold comprises lowering the alarm threshold for each individual physiological parameter relating to a condition for which the patient is being treated.

6. The method of claim 1 wherein the step of altering the alarm limits comprises raising or lowering the alarm threshold in relation to historical movement data for the patient.

7. The method of claim 1 wherein the step of altering the alarm limits comprises raising or lowering the alarm threshold in relation to a distance of medical personnel in relation to the patient.

8. The method of claim 1 wherein the step of altering the alarm limits comprises raising or lowering the alarm threshold in relation to a treatment being actively provided to the patient.

9. The method of claim 1 wherein the step of verifying the alarm condition by employing the at least one reactive input comprises soliciting a response from the patient after determining the existence of the alarm condition.

10. The method of claim 9 wherein the step of soliciting a response from the patient comprises actively querying the patient.

11. The method of claim 10 wherein the step of actively querying the patient comprises prompting the patient to provide an audible response.

12. The method of claim 9 wherein the step of soliciting a response from the patient comprises indirectly querying the patient.

13. The method of claim 9 further comprising the step of providing a primary alarm indication concurrently with soliciting a response from the patient.

14. The method of claim 13 further comprising the step of providing a secondary alarm indication if no response is received from the patient.

15. The method of claim 14 wherein the primary alarm indication is a visual-only indication.

16. The method of claim 14 wherein the secondary alarm indication is an audio-visual indication.

17. A monitoring device operable to provide information on data obtained from sensors operably connected between a patient and the device, the device comprising:

a) a central processing unit configured to receive incoming data signals from a sensors connected to the central processing unit concerning multiple physiological parameters of the patient and to compare the incoming data signals to a predetermined alarm threshold for each individual physiological parameter to determine an alarm condition; and b) electronic storage media operably connected to the central processing unit and selectively operable to store one or more proactive inputs concerning the adjustment of the alarm threshold for each individual physiological parameter and to store one or more reactive inputs used to verify a determined alarm condition, wherein the central processing unit is configured to automatically employ the one or more proactive inputs to alter the alarm threshold for each individual physiological parameter for determining a corresponding alarm condition without adjusting the data signals for the physiological parameters, and to automatically employ the one or more reactive inputs to verify any alarm condition determined relative to a physiological parameter.

18. The monitoring device of claim 17 further comprising a location sensor on medical personnel monitoring the patient and wherein the central processing unit is configured to alter the value of the alarm threshold for each individual physiological parameter in response to the a position of the location sensor.

19. The monitoring device of claim 17 wherein the central processing unit is configured to automatically solicit a response from the patient in a form contained in the reactive input upon the determination of an alarm condition by the central processing unit.

20. A medical monitoring device for providing information about a patient operably connected to the device, the device comprising:

a) an electronic storage medium in which values for alarm thresholds for a number of physiological parameters to be monitored are stored;

b) a central processing unit operably connected to the electronic storage medium and configured to receive incoming data signals concerning the parameters of the patient and to compare the incoming data signals to the alarm limits for the parameters to determine an alarm condition;

c) one or more sensors operably connected to the central processing unit and adapted to be connected to the patient to obtain and transmit the incoming data signals on the parameters to be monitored from the patient to the central processing unit; and d) a display operably connected to the central processing unit, the display including a display screen and a user interface configured to enable a number of proactive inputs and a number of reactive inputs to be stored in the electronic storage medium, wherein the central processing unit is configured to dynamically alter the alarm threshold for at least one physiological parameter in response to the proactive inputs and subsequently verify any detected alarm condition concerning a physiological parameter by employing the reactive inputs.

* * * * *